United States Patent [19]

Turbe

[11] Patent Number: 4,700,574
[45] Date of Patent: Oct. 20, 1987

[54] ULTRASONIC DETECTION METHOD OF THE INTERNAL DEFECTS OF A RAILROAD TRACK RAIL LOCATED IN THE SIDES OF THE HEAD OF SAID RAIL AND DEVICE TO CARRY IT OUT

[75] Inventor: Jean-Pierre Turbe, Nanteuil les Meaux, France

[73] Assignee: Matix Industries, Paris, France

[21] Appl. No.: 863,683

[22] Filed: May 15, 1986

[30] Foreign Application Priority Data

May 15, 1985 [CH] Switzerland ............... 02087/85

[51] Int. Cl.$^4$ ............................................. G01N 29/04
[52] U.S. Cl. .................................................. 73/636
[58] Field of Search ......................................... 73/636

[56] References Cited

U.S. PATENT DOCUMENTS

| | | | |
|---|---|---|---|
| 3,962,908 | 6/1976 | Joy | 73/636 |
| 4,174,636 | 11/1979 | Pagano | 73/636 |
| 4,487,071 | 12/1984 | Pagano et al. | 73/636 |

FOREIGN PATENT DOCUMENTS

WO82/03920  11/1982  PCT Int'l Appl. .
697918  11/1979  U.S.S.R. .................. 73/636

OTHER PUBLICATIONS

"Fatigue Crack Growth and Fracture Mechanics Considerations for Flaw Inspection of Railroad Rail", Steele, *Materials Evaluation*, Oct. 1980, pp. 33–38.

Primary Examiner—Howard A. Birmiel
Attorney, Agent, or Firm—Young & Thompson

[57] ABSTRACT

An ultrasonic beam is made to penetrate into the rail from the median surface (A) of the rolling table of the rail along a direction forming in horizontal projection an angle ($\alpha_1$) comprised between 10° and 25° with the longitudinal axis of the rail and in vertical projection an angle ($\alpha_2$) with the symmetric plane of the rail comprised between 60° and 80°. The echoes reflected by a displaced oval flaw are detected either directly or indirectly.

4 Claims, 13 Drawing Figures

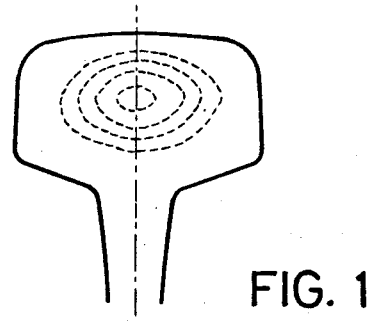
FIG. 1
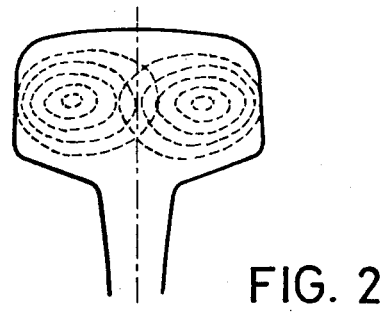
FIG. 2
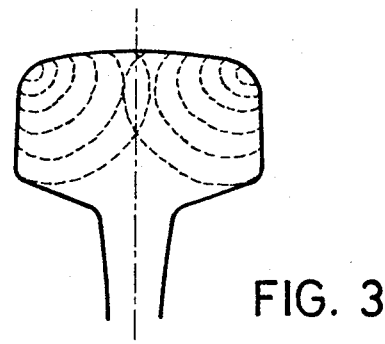
FIG. 3
FIG. 4
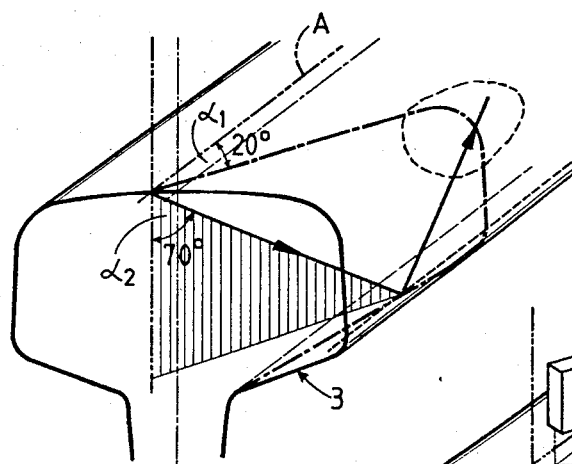
FIG. 5
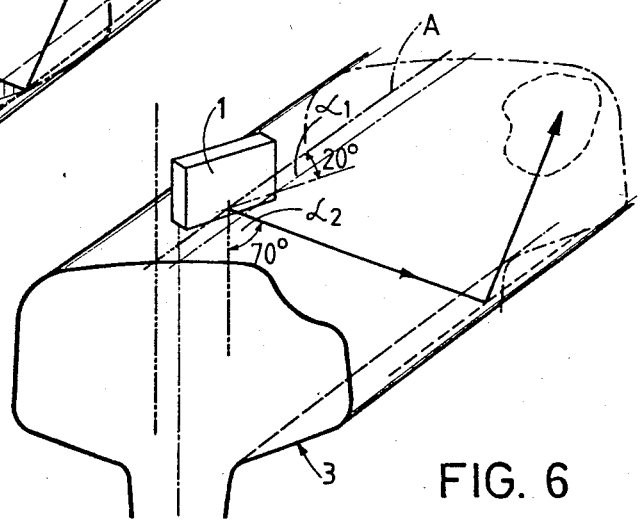
FIG. 6

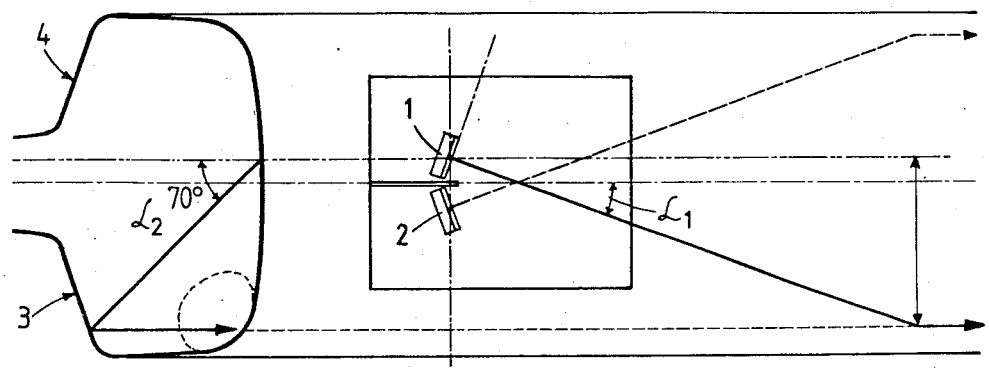
FIG. 7
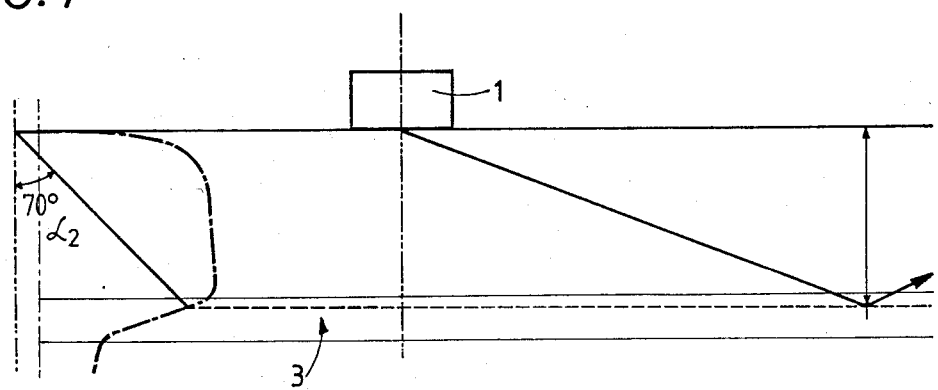
FIG. 8
FIG. 9
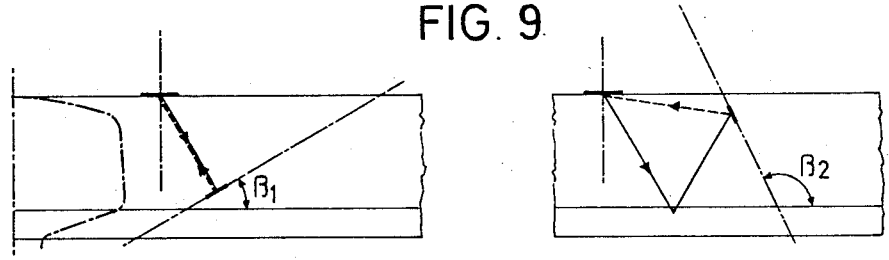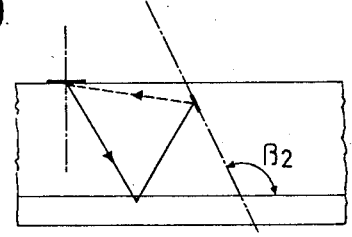
a                    b
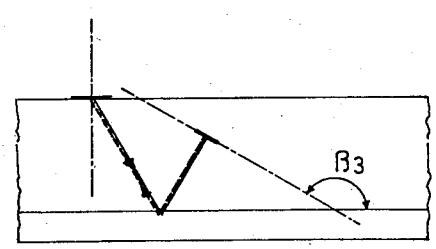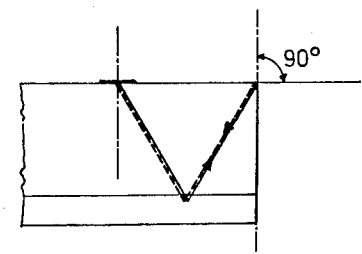
c                    d

ULTRASONIC DETECTION METHOD OF THE INTERNAL DEFECTS OF A RAILROAD TRACK RAIL LOCATED IN THE SIDES OF THE HEAD OF SAID RAIL AND DEVICE TO CARRY IT OUT

BACKGROUND OF THE INVENTION

Transverse cracks in the head of a rail generally develop in the median axis of the rail, as shown in FIG. 1. These well known cracks are called oval flaws.

These defects arise during manufacture, wherein a non homogenous core can, later on, give rise to a small crack which then propagates and gets bigger.

Rails on which trains travel undergo enormous stresses that enlarge these cracks which can extend over 100% of the rail cross-section, but ruptures of the rail, at the location of these cracks, may occur with cracks having a cross-sectional area as little as 20% of the rail, according to the circumstances (track, traffic).

Detection of these cracks is made by ultrasonic techniques. An ultrasonic beam having a refracted angle within the steel of 70° is directed toward the core of the head of the rail from a transducer placed on the rolling table of the rail. The energy which is reflected by the crack is detected and then measured by electronic circuits.

The operator can then take the necessary measures as a function of the significance of the detected cracks. He may observe the rail in question if it has small cracks or ask for its replacement in the case of big cracks.

Transverse cracks displaced either right or left of the median part of the head of the rail on either side of its symmetry axis, as shown in FIG. 2, have been known for several years.

Other transverse crackings propagate from the upper left and right corners of the head of the rail (FIG. 3).

The origin of these displaced cracks may be due to the type of rail itself, to the load per rolling axle of the trains and to the evolution of the steels used for the manufacture of the rails.

In certain countries, the phenomenon of FIG. 2 is of great occurrence and in other countries it is that of FIG. 3 which occurs most often.

In each of these cases there is the problem of the detection of displaced oval flaws.

At present detection of these displaced oval flaws (FIGS. 2 and 3) cannot be effected with precision and certainty. As a matter of fact, using the known methods, which were developed for the detection of the centered oval flaws (FIG. 1) one can never be sure of the nature of the flaws: for a given echo, was it reflected by a centered oval flaw of a certain amplitude or by one or several displaced oval flaws, of a different magnitude? This ambiguity in the measurement cannot be dealt with by the means now available and leads to a great risk of rupture or to the premature replacement of rails if one does not want to take any risks.

Furthermore, as seen in FIG. 4, the surface of the head of the rail is ordinarily deformed at its sides through the wearing off caused by the rolling of trains. Therefore, it is not possible to use ultrasonic emitting transducers which rest against the edges B and C of the head of the rail in order to try to detect the displaced oval flaws, because as the contact with the rail is not adequately realized in these places, the precision of the measure would be insufficient due to the fact that one would not obtain a good acoustic contact due to the shapes of the transducer and of the rail and therefore the trajectory of the ultrasonic beam in the rail would not be known with precision.

SUMMARY OF THE INVENTION

The present invention seeks to enable the measurement of displaced oval flaws by ultrasonic means using one or several emitter-receiver transducers resting on the median part A of the rolling surface of the head of the rail, which median surface is not deformed. It is only in this manner that it is possible to ensure a good accoustic contact between the transducer and the rail and thus to know the path and orientation of the beams emitted within the rail.

The detection method by use of ultrasonic means, of the displaced cracks of the head of a railroad rail distinguishes itself by the characteristics described in detail hereinafter.

The present invention has further for its object a device to carry out the method.

BRIEF DESCRIPTION OF THE DRAWINGS

The accompanying drawings show schematically and by way of example the working principle of the detection method according to the invention and two embodiments of the device to carry it out.

FIGS. 1-3 show the typical locations of oval flaws in rail heads.

FIG. 4 shows the shape of a worn rail.

FIGS. 5, 6, 7 and 8 show schematically the principle of the detection method, the location of the transducers, and the direction of travel of the ultrasonic beam with respect to the rail.

FIGS. 9a, b, c, d, show by way of example four possible reflection cases of an ultrasonic beam.

DETAILED DESCRIPTION OF THE INVENTION

Figure 10:
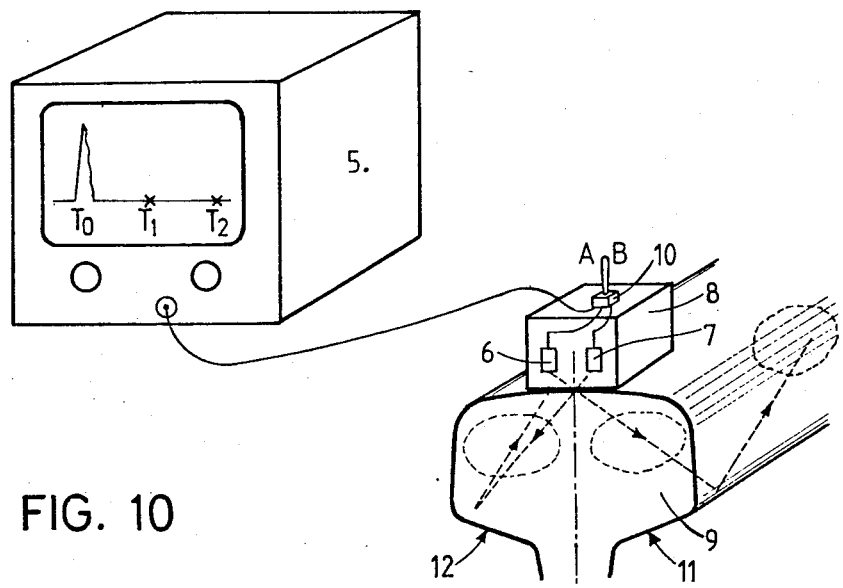
FIG. 10 shows a first embodiment of a device to carry out the detection method.

The method defined takes account of several parameters inherent to the shape of the head of the rail. The head of the rail comprises on its upper portion and on its sides natural curves which are designed to enable a good adaptation of a train wheel to the rail.

Furthermore, this rolling table wears off as a function of the number of millions of tons which it supports due to the passage of trains.

FIG. 4 shows a rail which, on its right side, has undergone a wearing off due to the friction on the rails and of their interconnection. This situation is often encontered in certain curved portions of the railroad track.

FIG. 4 also shows a rail which, at its left side, has undergone a flattening of the rolling table.

All these reasons militate against using the lateral portions B and C left and right of the rolling table to transmit the ultrasonic beams.

FIGS. 5 to 8 show the location and the directions of the ultrasonic beams employed.

The ultrasonic energy is transmitted from two distinct transducers. One beam is directed from the left to the right into the rail head and the other is directed from the right to the left from the median portion A of the rolling table.

The angle formed between the longitudinal median axis of the head of the rail and a horizontal projection of the beam is about $\alpha_1 = 20°$.

The angle formed between the vertical median axis of the rail and a vertical projection of the beam is of the order of $\alpha_2 = 70°$.

These angles are determined as a function of the inclination of the rail shoulder to obtain a good reflection and a propagation of the beam within a plane substantially parallel to the symmetry plane of the rail.

Taking into account the diverging of the beam into the steel:

$$\sin \alpha_{div.} = 1.2\lambda/D$$

where
$\lambda = c/f = 3230$ m/s/3 mhz and
$D = 16$ mm $$\alpha \neq 5°$$

where
div = diverging
$\lambda$ = wave length
D = diameter of the beam.

This diverging of the beam occurs symmetrically relative to the axis of the beam: thus the beam gets increasingly conical, The reflection of these conical beams on the inclined fishplates generates large beams which respectively traverse all of the right and left parts of the head of the rail.

The transverse cracks reflect the received energy directly or indirectly after reflection on these cracks, the rolling table, and the lateral portion of the head of the rail or the fishplates.

This detection method enables positioning the emitter-receiver ultrasonic transducers 1, 2 so that they bear on the median portion of the rolling table of the head of the rail, to emit ultrasonic beams into the rail forming in horizontal projection an angle $\alpha_1$ comprised between 10° and 25° with the longitudinal axis of the head of the rail and in vertical projection an angle $\alpha_2$ comprised between 60° and 80° with the vertical axis of the rail. By doing so these beams, which become conical due to their diverging in the steel, are reflected by the corresponding fishplates 3,4 and traverse all the volume, respectively, of the left part and right part of the head of the rail, thus permitting the detection of any displaced oval flaws.

These two emitter-receiver transducers 1, 2 are generally mounted in the same support that is adapted to slide on the rolling surface of the rail, which support is displaced along the rail in order to check the whole length of it. It is evident that a third transducer can be mounted in this support, emitting a central ultrasonic beam in the plane of the longitudinal axis of the head of the rail, simultaneously to detect the centered oval flaws (FIG. 1).

The distances traveled by these ultrasonic waves are sufficiently long (300 mm to go and return) and depend on the height of the head of the rail.

The energy returned to the transducers is amplified and analysed.

The energy emitted at time To (FIG. 12) is transmitted into the steel of the head of the rail toward the right portion and left portion of the cross-section of the head of the rail, respectively, and rebounds on the fishplate. If there is a crack, an energy is reflected back and travels along the reverse path. The wave travels this path at the speed of 3230 meter/second. When the transducer is displaced and a crack is located in the space where the rebound of the wave takes place, there is, due to the diverging of the beam, a direct or indirect reflection which appears on the oscillogram at times $T_1$ or $T_2$.

Electronic circuits detect the energies at times $T_1$ and $T_2$

FIG. 9a shows the case of a displaced oval flaw inclined at an angle $\beta_1$ (20° to 30°) with respect to a plane parallel to the rolling table, which causes a direct reflection of the incident beam before it reaches the fishplate.

FIG. 9b shows the case of a displaced oval flaw inclined at an angle $\beta_2$ (110° to 130°) with respect to a plane parallel to the rolling table of the rail, which causes an indirect reflection of the incident beam after said beam has rebounded on the fishplate.

FIG. 9c shows the case of a displaced oval flaw inclined at an angle $\beta_3$ (150° to 160°) with respect to a plane parallel to the rolling table of the rail, which causes an indirect reflection of the incident beam after its rebound on the fishplate. Here the reflected beam also rebounds on the fishplate during its return travel.

Finally, FIG. 9d shows the case of a rail end inclined 90° with respect to a plane parallel to the rolling table of the rail, which causes an indirect reflection of the incident beam after its rebound on the fishplate. This reflection is created by the high corner formed by the rolling table and the rail end.

In each of the above described cases, the propagation and return paths travelled by the ultrasonic beam have a different length so that it is possible by measuring the time interval separating the emission of the ultrasonic impulsion from the reception of an echo to know which type of crack, and its position and inclination, has been detected.

In practice, one creates electronically a window $F_1$ during which the echos obtained by configurations according to FIGS. 9a and 9b will be received, and a second window $F_2$ (FIG. 12) during which echoes obtained by the configurations of FIGS. 9c and 9d are received. Outside of these time intervals $F_1$, $F_2$ the echos are not taken into consideration.

The method thus permits by means of ultrasonic transducers guided along the rolling surface of the head of the rail not only to detect the displaced oval flaws located in the sides of the rail head, but also to determin their nature and, as will be seen later on, their differentiation with respect to rail ends.

FIG. 10 shows a first embodiment of a manual detecting device for carrying out the detection method described. This device comprises a standard ultrasonic apparatus having one transmission-reception channel provided with a cathodic display. The electronic portion 5 delivers signals to two ultrasonic emitter-receiver transducers 6, 7 mounted in a support 8. This support 8 comprises a contact surface intended to be laid onto the rolling table of the rail head 9 so that the transducers be in sonic contact with the rail. When the support is in service position laid on the rolling table of the rail, the transducers 6, 7 are located on either side of the longitudinal symmetry plane of the head of the rail 9 and directed in such a way that the ultrasonic beam emitted by the transducer 6, located on the left of said median plan, traverses the right portion of the head of the rail 9 and that the ultrasonic beam emitted by the transducer 7, located on the right side of said median plane, traverses the left portion of the head of the rail. These incident beams, which are directed into the rail along angles $\alpha_1$ and $\alpha_2$ as described here above, rebound on the fishplates 11, 12 and give rise to echoes when they fall on displaced oval flaws.

The two transducers 6, 7 are fed simultaneously by signals coming from the electronic part 5 and thus simultaneously emit incident discontinuous ultrasonic beams into the rail. A commutator 10 enables disconnecting the transducer 6 or the transducer 7.

The support 8 is linearly displaced along the rolling table of the rail at a speed determined in such a way that, taking account the scanning frequency of the emission of ultrasonic impulses, a 100% check of the rail can be performed.

If a pulse is emitted at time To, the transducers can receive echos at times $T_1$ or $T_2$ when the pulses is reflected by an oval flaw depending on whether the reflection is direct or indirect receiving an echo, the user makes the support stand still and isolates the transducer 6 or the transducer 7 by means of the inverter 10. In such a way, it is possible to know if the echo is caused by the reflection of the beam emitted by the transducer 6 or the transducer 7 and it is thus possible to determine on which side of the head of the rail the defect causing the echo is located. If the echo is simultaneously detected with the same energy regardless of which transducer is in service, this will indicate detection of a rail end or an oval flaw of very great extent which would cover nearly all the surface of the head of the rail. The operator can very easily see the difference between a rail end and an internal defect of the rail head.

In such an embodiment, the design of the electronic apparatus as well as the one of the transducers is conventional. What is new is the geometrical orientation of the transducers 6, 7 within the support such that when this is in service position applied against the rolling surface of the rail the incident ultrasonic beams are emitted within the rail along the angles $\alpha_1$ and $\alpha_2$ described here above and that each of these incident beams intersects the median plan of the rail.

In a variant it is evident that the transducers 6, 7 may be fed alternatively so that it will be possible to attribuate the received echoes, as a function of the time interval separating their emission, to one or the other transducer and thus to know on which side of the median plane of the rail the defect is located.

Figure 11:
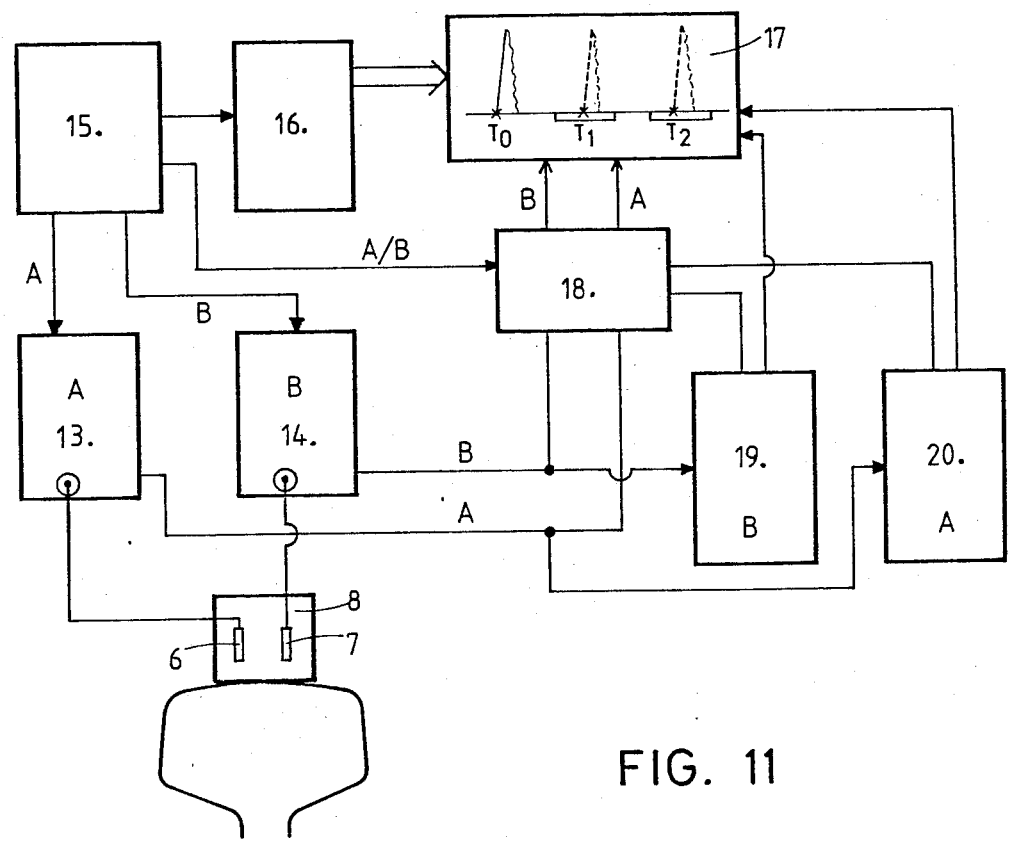
FIGS. 11, 12 and 13 show a second embodiment of the detection device according to the invention.

When it is necessary to systematically check a greater length of rail one has to have an automatic apparatus mounted for example on a measuring railroad vehicle displacing itself along a portion of the track to be checked. FIG. 11 shows schematically such an automatic detection device.

This automatic installation for the detection by ultrasonic means comprises a housing or support 8 similar to the one of the first embodiment shown, mounted on a driven carriage or truck of a railroad vehicle, housing the two emitter-receiver transducers 6, 7 directed with respect to the rail in the same way as described above.

The transducer 6 is connected to an emitter-receiver 13 whereas the transducer 7 is connected to an emitter-receiver 14. These two emitter-receivers 13, 14 are controlled by a phase commutator 15 so that when the channel A is in emitting mode, the channel B is out of service and vice-versa. Therefore in this example, the transducers 6, 7 work alternately.

The phase commutator 15 is further connected to a time base 16 controlling the scanning of the horizontal axis of a display device 17 constituted either by a recorder or by a cathodic video screen. This phase commutator is also controls an inverter 18 receiving the reception signals of the two channels A and B, since it is connected to the emitters-receivers 13 and 14 and delivers to the display device 17 a signal referring to one of these channels A and B respectively. This inverter 18 is controlled by the phase commutator 15 in such a way that it is also the reception signal of the activated transducer which is delivered to the display 17.

Figure 12:
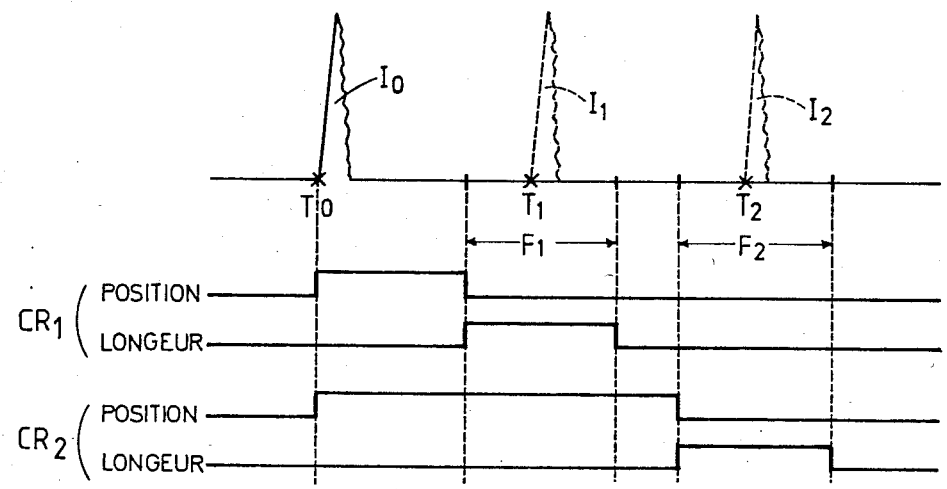

Finally, this device further comprises two receiving time selectors 19, 20 which permit displaying on the display device 17 the windows $F_1$, $F_2$ corresponding to time intervals within which, for a given transducer, the direct and indirect echoes may be received, respectively. FIG. 12 shows an emitted pulse Io at time To which, if a defect is detected, gives rise according to the propagation mode (FIGS. 9a, b, or 9c, d) of the ultrasonic emissions within the rail, to echoes $I_1$ and $I_2$ at times $T_1$ and $T_2$ respectively. To avoid any parasitic echo, the measuring device is inhibited outside of the windows $F_1$, $F_2$ or the time interval during which these echoes are received.

Figure 13:
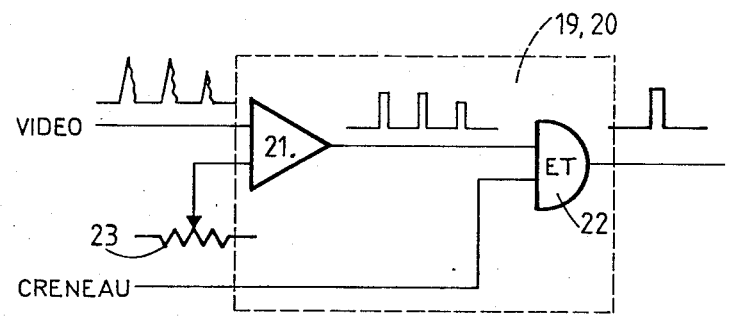

FIG. 13 shows a diagram of such a selector 19, 20 comprising an amplifier 21 receiving the signals caused by the echoes and a shaping circuit 23. This amplifier eliminates the signals of an amplitude lower than a given value and transforms the received pulses into rectangular pulses. These rectangular pulses are delivered to an AND gate 22 the other input of which receives a signal determining the position and the duration of the passing window ($F_1$, $F_2$). On the output of this AND gate corresponding to the output of the selector 19 and 20 remain only the pulses corresponding to echoes received during the time interval $F_1$ and $F_2$, respectively. These time intervals $F_1$, $F_2$ are determined as a function of the dimensions of the rail head.

With such a detecting installation, by choosing the repetition frequency of the emitted impulses and the displacement speed of the support 8 along the rail in such a way that one pulse is emitted every 4 mm with ultrasonic beams having a diameter of about 16 mm, one realizes ideal conditions to make a 100% check of the rail.

It is to be noted that the different elements and electronic components used are well known but here also the originality resides in the particular disposition of the transducers 6, 7 which permit the detection of displaced oval flaws while resting on the rolling table of the rail.

It is evident that the support of the housing could comprise a third ultrasonic emitter-receiver transducer, the beam of which would be directed parallel to the longitudinal axis of the rail, simultaneously to detect the centered flaws.

I claim:
1. A method for ultrasonic detection of displaced oval flaws in a rail head having a median plane of symmetry, comprising the steps of:
displacing a support in sliding contact with a rail head along said median plane at a constant rate of speed, said support comprising a pair of ultrasonic emitter-receivers symmetrically disposed on opposite sides of said median plane such that each said emitter-receiver is adapted to emit across said median plane an ultrasonic beam of constant orientation having a vertical projection forming an angle of 60°–80° on said median plane and a horizontal pro- jection forming an angle of 10°-25° relative to said median plane;

alternately emitting ultrasonic beams from each of said pair of ultrasonic emitter-receivers;

receiving an echo of a said emitted ultrasonic beam reflected by a displaced oval flaw in said rail head; and determining on which side of said median plane said displaced oval flaw is located, based on a time difference between the corresponding said alternate emission and its reception by one of said pair of emitter-receivers.

2. A method according to claim 1, wherein time windows are established outside of which no said echo is received, a first said time window receiving echoes generated by direct reflection of a said ultrasonic beam and a second said time window receiving echoes generated by indirect reflection of a said ultrasonic beam; and a said oval flaw is detected having an orientation within said rail head defined by in which of said first and second time windows its corresponding echo appears.

3. Apparatus for ultrasonic detection of displaced oval flaws in a rail head having a median plane of symmetry comprising:

means for displacing a support in sliding contact with a rail head along said median plane at a constant rate of speed, said support comprising a pair of ultrasonic emitter-receivers symmetrically disposed on opposite sides of said median plane such that each said emitter-receiver is adapted to emit across said median plane an ultrasonic beam of constant orientation having a vertical projection forming an angle of 60°-80° on said median plane and a horizontal projection forming an angle of 10°-25° relative to said median plane;

means for alternately emitting ultrasonic beams from each of said pair of ultrasonic emitter-receivers;

means for receiving an echo of a said emitted ultrasonic beam reflected by a displaced oval flaw in said rail head; and means for determining on which side of said median plane said displaced oval flaw is located, based on a time difference between the corresponding said alternate emission and its reception by one of said pair of emitter-receivers.

4. Apparatus according to claim 3, and means for establishing time windows outside of which no said echo is received, a first said time window receiving echoes generated by direct reflection of a said ultrasonic beam and a second said time window receiving echoes generated by indirect reflection of a said ultrasonic beam; and means for detecting a said oval flaw having an orientation within said rail head defined by in which of said first and second time windows its corresponding echo appears.

* * * * *